US00PP21526P2

(12) United States Plant Patent
Heuger

(10) Patent No.: US PP21,526 P2
(45) Date of Patent: Nov. 23, 2010

(54) ***HELLEBORUS* PLANT NAMED 'HLR 140'**

(50) Latin Name: *Helleborus orientalis*
Varietal Denomination: HLR 140

(76) Inventor: Josef Heuger, Postfach 11 03, D-49215 Glandorf (DE)

( * ) Notice: Subject to any disclaimer, the term of this patent is extended or adjusted under 35 U.S.C. 154(b) by 0 days.

(21) Appl. No.: 12/459,839

(22) Filed: Jul. 8, 2009

(51) Int. Cl.
*A01H 5/00* (2006.01)

(52) U.S. Cl. ..... Plt./439

(58) Field of Classification Search ..... Plt./439
See application file for complete search history.

*Primary Examiner*—June Hwu
(74) *Attorney, Agent, or Firm*—C. A. Whealy

(57) ABSTRACT

A new and distinct cultivar of *Helleborus* plant named 'HLR 140', characterized by its upright plant habit; freely flowering habit; long flowering period; single light pink and greyed purple bi-colored flowers; and good garden performance.

2 Drawing Sheets

Botanical designation: *Helleborus orientalis.*
Cultivar denomination: 'HLR 140'.

BACKGROUND OF THE INVENTION

The present invention relates to a new and distinct cultivar of *Helleborus* plant, botanically known as *Helleborus orientalis*, and hereinafter referred to by the name 'HLR 140'.

The new *Helleborus* plant is a product of a planned breeding program in Glandorf, Germany. The objective of the breeding program was to create new uniform *Helleborus* cultivars with unique and attractive flower coloration and resistance to pests.

The new *Helleborus* plant originated from a cross-pollination conducted by the Inventor in Glandorf, Germany in November, 2002 of two unnamed proprietary seedling selections of *Helleborus orientalis*, not patented. The new Helleborus plant was discovered and selected by the Inventor as a single flowering plant from within the progeny of the stated cross-pollination grown in a controlled greenhouse environment in Glandorf, Germany in February, 2005.

Asexual reproduction of the new *Helleborus* plant by divisions in a controlled greenhouse environment in Glandorf, Germany since March, 2005, has shown that the unique features of this new *Helleborus* plant are stable and reproduced true to type in successive generations.

SUMMARY OF THE INVENTION

Plants of the new *Helleborus* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'HLR 140'. These characteristics in combination distinguish 'HLR 140' as a new and distinct cultivar of *Helleborus:*

1. Upright plant habit.
2. Freely flowering habit.
3. Long flowering period.
4. Single light pink and greyed purple bi-colored flowers.
5. Good garden performance.

Compared to plants of the parent selections, plants of the new *Helleborus* are more uniform and more freely flowering.

Plants of the new Helleborus can be compared to plants of *Helleborus orientalis* 'HGC Merlin', disclosed in U.S. Plant Pat. No. 15,705. Plants of the new *Helleborus* differ primarily from plants of 'HGC Merlin' in the following characteristics:

1. Plants of the new *Helleborus* have larger flowers than plants of 'HGC Merlin'.
2. Flowers of plants of the new *Helleborus* are light pink and greyed purple in color whereas flowers of plants of 'HGC Merlin' are dark purple in color.

BRIEF DESCRIPTION OF THE PHOTOGRAPHS

The accompanying colored photographs illustrate the overall appearance of the new *Helleborus* plant, showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet comprises a side perspective view of a typical flowering plant of 'HLR 140' grown in a container.

The photograph on the second sheet is a close-up view of a typical flower of 'HLR 140'.

DETAILED BOTANICAL DESCRIPTION

The aforementioned photographs and following observations, measurements and values describe plants grown in Glandorf, Germany in 1.5-liter containers during the winter in a glass-covered greenhouse and under conditions which closely approximate commercial *Helleborus* production. During the production of the plants, day temperatures ranged from 12° C. to 32° C. and night temperatures ranged from 3° C. to 18° C. Plants were one year old when the photographs and the description were taken. In the following description, color references are made to The Royal Horticultural Society Colour Chart, 2007 Edition, except where general terms of ordinary dictionary significance are used.

Botanical classification: *Helleborus orientalis* 'HLR 140'.

Parentage:

*Female, or seed, parent.*—Unnamed proprietary seedling selection of *Helleborus orientalis*, not patented.

*Male, or pollen, parent.*—Unnamed proprietary seedling selection of *Helleborus orientalis*, not patented.

Propagation:

*Type.*—By tissue culture.

*Time to initiate roots.*—About two months at 12° C.

*Time to produce a rooted young plant.*—About six months at 4° C. to 15° C.

*Root description.*—Thick to thin, fleshy; white to brown in color.

*Rooting habit.*—Sparse.

Plant description:

*Plant form and growth habit.*—Herbaceous perennial; upright plant habit; moderately vigorous growth habit.

*Plant height.*—About 43.9 cm.

*Plant diameter* (*area of spread*).—About 32.2 cm.

Foliage description:

*Arrangement.*—Palmately compound with five leaflets per leaf.

*Leaf length.*—About 15.5 cm.

*Leaf width.*—About 14.7 cm.

*Leaflet length.*—About 9.4 cm.

*Leaflet width.*—About 3.7 cm.

*Leaf shape.*—Palmate; orbicular in outline.

*Leaflet shape.*—Obovate; lowest leaflets cleft to three-parted.

*Leaflet apex.*—Acute.

*Leaflet base.*—Attenuate.

*Leaflet margin.*—Sharply senate.

*Leaflet texture, upper and lower surfaces.*—Smooth, glabrous; leathery.

*Leaflet venation pattern.*—Pinnate.

*Leaflet color.*—Developing leaves, upper surface: Between 143A and 147A. Developing leaves, lower surface: Close to 146A. Fully developed leaves, upper surface: Slightly darker than N137A; venation, close to 144A. Fully developed leaves, lower surface: Between 146B and 147B; venation, close to 144B.

*Petiole.*—Length: About 14.3 cm. Diameter: About 4 mm. Texture, upper and lower surfaces: Smooth, glabrous. Color, upper and lower surfaces: Close to 144A; towards the base, tinged with close to 177A.

Flower description:

*Flower shape and habit:.*—Single rotate flowers; freely flowering habit, about eleven flowers developing per plant; petals not observed.

*Fragrance.*—None detected.

*Natural flowering season.*—Long flowering period; plants flower from January to March in Germany.

*Flower longevity on the plant.*—About twelve days; flowers not persistent.

*Flower buds.*—Length: About 2 cm. Diameter: About 1.5 cm. Shape: Ovate. Color: Close to 182C; towards the base, between 144C and 145A to 145B; venation, close to 187A to 187B.

*Flowers.*—Diameter: About 5 cm. Depth (height): About 3.5 cm.

*Sepals.*—Arrangement: About five in a single whorl. Length: About 3.8 cm. Width: About 4.1 cm. Shape: Orbicular. Apex: Rounded to slightly acute. Margin: Entire. Texture, upper and lower surfaces: Smooth, glabrous; waxy. Color: When opening, upper surface: Towards the margins, between 69D and 76D; central blotch, close to 187A to 187B. When opening, lower surface: Close to 76D; venation, close to 183A. Fully opened, upper surface: Towards the margins, close to 75D; central blotch, close to 187A to 187B; with development, color becoming closer to 145B towards the margins and central blotch, close to N77B to N77C. Fully opened, lower surface: Close to 75D; venation, close to 183A.

*Primary peduncles.*—Strength: Moderately strong. Length: About 40.6 cm. Diameter: About 8 mm. Aspect: Mostly upright, about 10° from vertical. Texture: Smooth, glabrous. Color: Close to 144B.

*Reproductive organs.*—Stamens: Quantity per flower: About 80. Filament length: About 1 cm. Filament color: Close to 145D. Anther shape: Reniform. Anther length: About 2 mm. Anther color: Close to 157D. Pollen amount: Moderate. Pollen color: Close to 155A to 155B. Pistils: Quantity per flower: About six. Pistil length: About 1.1 cm. Stigma shape: Club-shaped. Stigma color: Close to 148A. Style length: About 1.1 cm. Style color: Close to 145B tinged with close to 177B to 177C. Ovary color: Close to 144B. Nectaries: Quantity per flower: About 15. Length: About 9 mm. Diameter, apex: Close to 4.5 mm. Diameter, base: Close to 1 mm. Color: Close to N144C; towards the apex, close to N144A; towards the base, close to 153A.

*Seeds/fruits.*—Seed and fruit development have not been observed.

Garden performance: Plants of the new *Helleborus* have been observed to have good garden performance and to tolerate rain and wind. Plants of the new *Helleborus* have been observed to tolerate high temperatures of about 35° C. and are hardy to USDA Hardiness Zone 5.

Pathogen/pest resistance: Plants of the new *Helleborus* have not been shown to be resistant to pathogens and pests common to *Helleborus.*

It is claimed:

1. A new and distinct *Helleborus* plant named 'HLR 140' as illustrated and described.

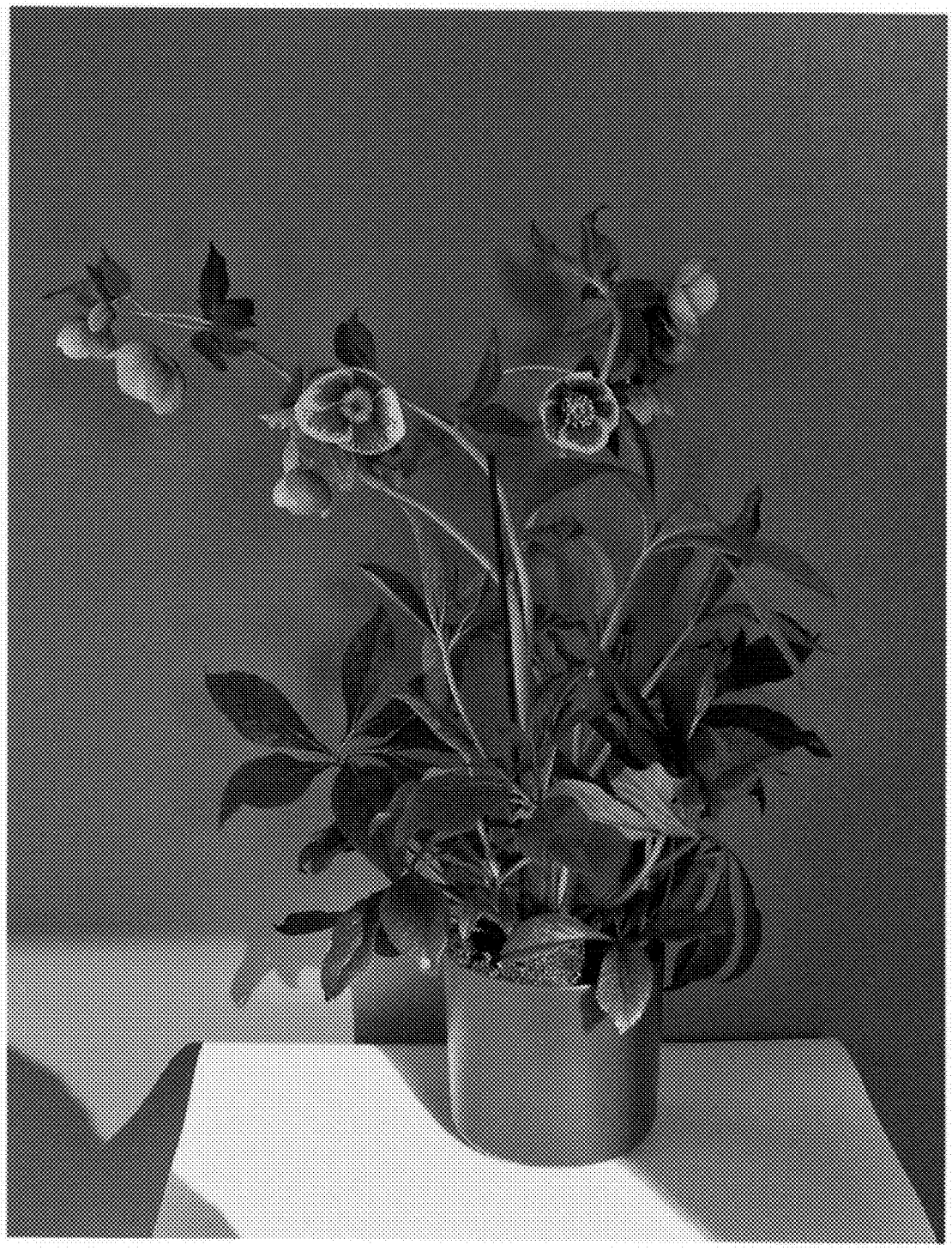

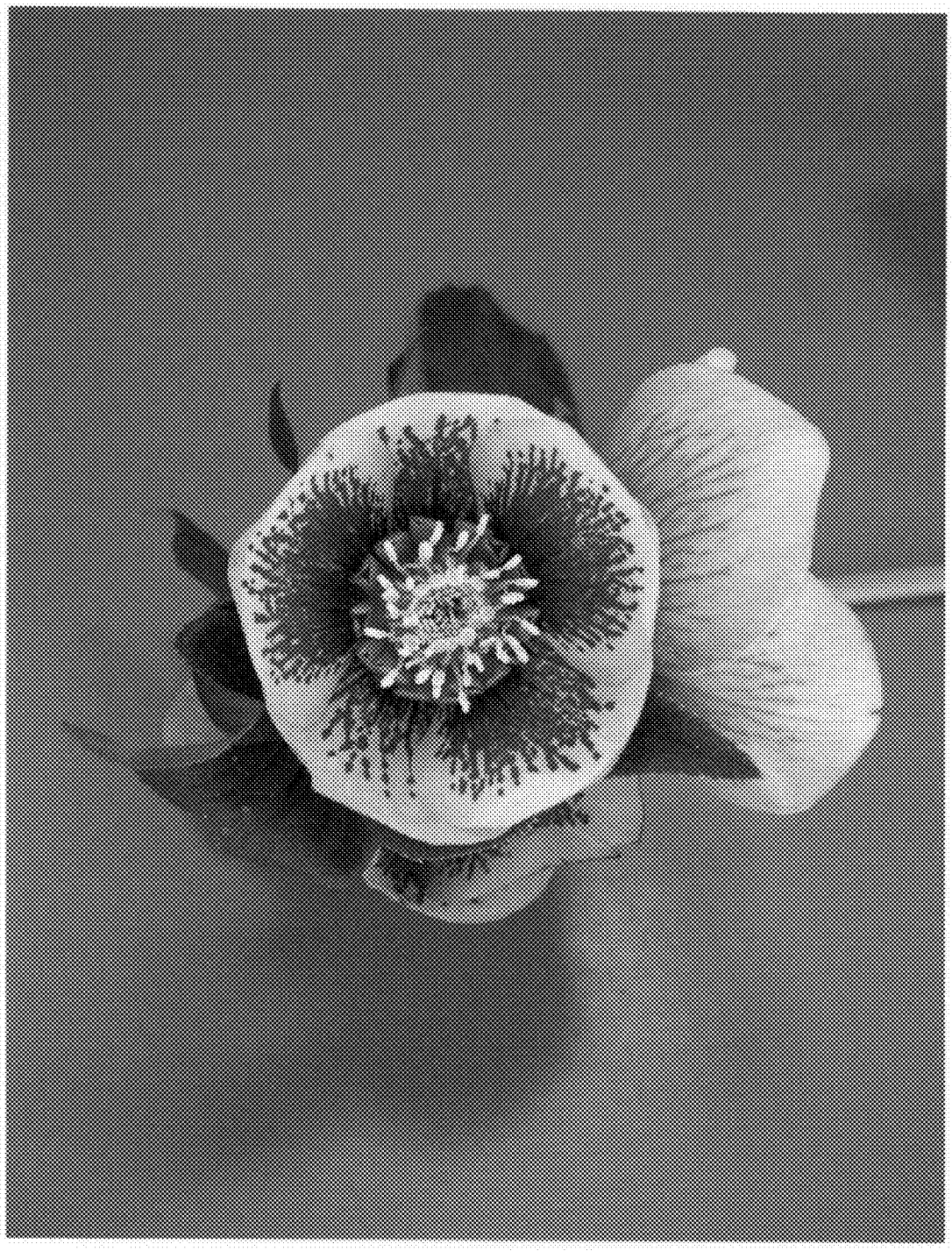

* * * * *